United States Patent [19]

Hsu

[11] Patent Number: 4,737,591

[45] Date of Patent: Apr. 12, 1988

[54] CATALYST AND PROCESS FOR PRODUCTION OF CINNAMATES

[75] Inventor: Chao-Yang Hsu, Media, Pa.

[73] Assignee: Sun Refining and Marketing Company, Philadelphia, Pa.

[21] Appl. No.: 684,822

[22] Filed: Dec. 21, 1984

[51] Int. Cl.$^4$ ............................................. C07C 69/76
[52] U.S. Cl. ...................... 560/104; 560/55; 560/21; 560/20; 560/75; 560/102
[58] Field of Search ..................... 560/104; 562/406

[56] References Cited

U.S. PATENT DOCUMENTS 3,346,625 10/1967 Fenton et al. .................. 562/406
3,381,030 4/1968 Biale et al. .................... 562/406
3,437,676 4/1969 von Kutepow .................. 562/406
3,530,168 9/1970 Biale ............................ 562/406

FOREIGN PATENT DOCUMENTS 7021342 2/1982 Japan ............................ 560/104

Primary Examiner—Paul J. Killos
Attorney, Agent, or Firm—J. Edward Hess; Donald R. Johnson

[57] ABSTRACT

A method of preparing esters of cinnamic acid comprising catalytically reacting a styrene compound with carbon monoxide, oxygen, and an aliphatic alcohol. The catalyst is essentially a combination of a palladium (II) compound and a copper salt. A catalytic amount of a dehydrating agent may be present to increase the selectivity of the reaction.

11 Claims, No Drawings

CATALYST AND PROCESS FOR PRODUCTION OF CINNAMATES

BACKGROUND OF THE INVENTION

The present invention relates to a catalytic process for preparing cinnamates by oxidative carbonylation of styrene compounds.

Cinnamic acid and cinnamates are used as a material for perfumes, as a cinnamic aldehyde, cyclamen aldehyde, beta-amyl cinnamic aldehyde, and the like.

Cinnamates are made conventionally through a Claisen condensation from benzaldehyde and alkylacetate in the presence of sodium alkoxide, as shown in Equation I

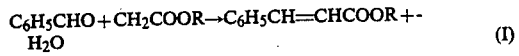

$$C_6H_5CHO + CH_2COOR \rightarrow C_6H_5CH=CHCOOR + H_2O \quad (I)$$

Another method of making cinnamates is by esterification of cinnamic acid, as shown in Equation II

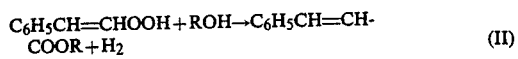

$$C_6H_5CH=CHOOH + ROH \rightarrow C_6H_5CH=CHCOOR + H_2 \quad (II)$$

Recently, several methods for preparing cinnamates have been reported, employing palladium catalysts. Heck et al., *J. Amer. Chem. Soc.* 91, 6707 (1969) and Patel et al., *J. Org. Chem.*, 42, 3903 (1977), show methods of preparing cinnamates using palladium acetate-tertiary phosphine as a catalyst in the reaction of phenyl bromide and an alkyl acrylate. This reaction has the drawback of involving rather expensive raw materials. This reaction is shown in Equation III.

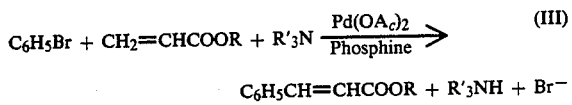

$$C_6H_5Br + CH_2=CHCOOR + R'_3N \xrightarrow{\underset{\text{Phosphine}}{Pd(OAc)_2}}$$

$$C_6H_5CH=CHCOOR + R'_3NH + Br^- \quad (III)$$

Other cinnamates, such as methyl cinnamate, can be synthesized in a palladium catalyzed reaction by reacting styrene with carbon monoxide and methanol, as reported by J. K. Stille and his coworkers, *J. Amer. Chem. Soc.*, 98, 1806 (1976) and 98, 1810 (1976); *J. Org. Chem.*, 44, 3474 (1979); and by G. Cometti and G. P. Chiusoli in *J. Organometal. Chem.*, 181, C14 (1979).

In Stille's method, methyl cinnamate could be obtained only in a small amount, with dimethyl phenylsuccinate being the major product. Additionally, a stoichiometric amount of copper (II) salt was required in this reaction. The method of Cometti and Chiusole has the same disadvantage of using a large excess of copper (II) salt as an oxidant. Thus, both methods are unsuitable for industrial applications.

Many patents disclose oxidative carbonylation of olefins to alpha, beta-unsaturated esters by reacting an olefin with carbon monoxide, oxygen, and an alcohol in the presence of a catalytic amount of palladium and copper salts, cf. U.S. Pat. Nos. 3,381,030; 3,397,225; 3,397,226; 3,530,168; 3,621,054. None of these patents discloses a satisfactory method for producing cinnamates.

Two Japanese patent applications, Nos. 21,342 (1982) and 21,343 (1982), disclose that low yields of methyl cinnamate could be achieved through oxidative carbonylation of styrenes, provided that an excess amount of dehydrating agent is used in the reaction. Because the dehydrating agent is an expensive component of the reaction, industrial application of this method is limited. It was disclosed in these two Japanese applications that when styrenes were allowed to react with aliphatic alcohols, carbon monoxide, and oxygen in the presence of palladium and a dehydrating agent, cinnamates could be obtained with a high reaction rate and a high yield. However, this reaction has the disadvantage of requiring an excess of dehydrating agent, which makes the reaction unfeasible for industrial use.

SUMMARY OF THE INVENTION

Cinnamates can be produced by the oxidative carbonylation of styrene compounds according to the following reaction, in the absence of dehydrating agent:

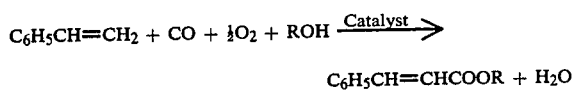

$$C_6H_5CH=CH_2 + CO + \tfrac{1}{2}O_2 + ROH \xrightarrow{\text{Catalyst}}$$

$$C_6H_5CH=CHCOOR + H_2O$$

It was unexpectedly found that when a styrene compound was reacted with carbon monoxide, oxygen, and an aliphatic alcohol and in the present of a catalytic amount of a palladium salt and a copper salt, high reaction rates and high yields of alkyl cinnamate could be obtained, along with valuable acetophenone as a by-product. Moreover, unlike the prior art reactions, this reaction can be carried out smoothly either without any dehydrating agent or using only catalytic amounts of dehydrating agent to increase the reaction rate and total yield of the alkyl cinnamates.

The present invention relates to a method for the oxidative carbonylation of styrenes to alkyl cinnamates by reacting styrenes with carbon monoxide oxygen, and aliphatic alcohols in the present of a catalyst consisting of a palladium salt and a copper salt. The general formula for styrenes for use in the present invention can be represented by the following structure:

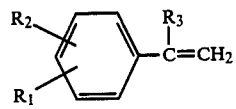

wherein $R_1$ and $R_2$ can be hydrogen, halogen, hydroxyl, alkyl, alkoxyl, aryl, aryloxy, or nitro functional groups. $R_3$ is an alkyl group of one to six carbon atoms. Specific examples for styrenes are styrene, alpha-methyl styrene, p-chloro styrene, p-nitro styrene, m-methoxy styrene, p-phenyl styrene, beta-methyl-p-isopropylstryene, beta-amylstyrene, and the like.

The aliphatic alcohols for use in the reaction according to the present invention include aliphatic alcohols having from one to six carbon atoms, such as methanol, ethanol, propanol, isopropanol, t-butanol, n-butanol, hexanol, and the like. It is also possible to use compounds capable of yielding the aforementioned alcohols in reaction systems containing acetals, ketals, orthoesters of carboxylic acids, dialkylcycloakanes, orthoboric acid esters, and the like.

Carbon monoxide and oxygen for this reacton can be used either in the pure state or can be mixed with nitrogen, argon, and other inert gases as the diluents. Air can be used as the oxygen source. In general, carbon monoxide and oxygen can be charged into the reactor through a separated inlet system or can be charged as a mixture with or without inert gases as the diluents. The partial pressure of carbon monoxide or oxygen is adjusted so that the gas mixture in the reactor system is outside the explosive range.

The catalyst consists of two components, a palladium salt and a copper salt. The palladium salt can be palladium chloride, palladium bromide, palladium iodide, palladium nitrate, or other divalent palladium salts such as palladium acetate, palladium benzoate, palladium acetylacetonate, palladium trifluoroacetate, palladium oxide, potassium tetrabromopalladate, sodium tetrachloropalladate, and the like. Any other forms of palladium which can form palladium (II) salt under the reaction conditions can be used. Examples are supported palladium such as palladium on carbon, palladium on silica, or palladium on alumina, palladium on silica-alumina, magnesia, titania, kieselguhr, active charcoal, graphite, etc., palladium black, and palladium sponge. Further example of useful palladium compounds are palladium alpha-picolinate, carboxylates of divalent palladium, bis(acetylacetonato)palladium, bis(triphenylphosphine)dichloro palladium, cyclooctadiene dichloropalladium, tetramine dichloro palladium, and the like.

The copper salts used in the reaction according to the present invention can be either copper (I) or copper (II) salts. Examples of these salts are copper (I) or (II) halides such as copper (II) fluoride, copper (I) chloride, copper (II) chloride, copper (I) bromide, copper (II) bromide, copper (I) iodide, and other non-halide coppers salts such as copper (II) nitrate, copper (II) acetate, and copper (II) sulfate.

The reaction temperatures can range from about 25° to 250° C., and the preferred temperature range is from about 50° C. to about 150° C.

Reaction pressures can range from about 1 to about 1500 psi, although ranges in the amount of about 50 to about 750 psi are preferred.

The gas composition, the molar ratio of carbon monoxide to oxygen, can range broadly from about 0.1 to 20. A molar ratio of carbon monoxide to oxygen of from about 0.25 to 10 is preferred.

The catalyst composition can range from a molar ratio of copper to palladium of about 1 to 50, although a molar ratio of copper to palladium of about 2.5 to 20 is preferred.

The molar ratio of styrene to palladium can range from about 10,000 to 10. A molar ratio of styrene to palladium of about 1000 to 25 is preferred.

The molar ratio of alcohol to styrene can range from 500 to 1, although a molar ratio of alcohol to styrene of form about 10 to about 1 is preferred.

Although the invention relates to a method of preparing cinnamic acid esters by catalytic carbonylation of a styrene compound with carbon monoxide, in the absence of a dehydrating agent, it has been discovered that catalytic amounts of dehydrating agent can be used to increase the selectivity of the reaction, to provide a greater percentage yield of cinnamic acid esters over the other products of the reaction. Although the total yield of desired products is reduced using a catalytic amount of dehydrating agent, it has been found that the increased selectivity of the reacton for the cinnamates may be a desired end.

Examples of dehydrating agents that can be used include dimethoxymethane, other acetals, 2.2-dimethoxypropane, other ketals, methyl orthoformate, ethyl orthoformate, isopropyl orthoformate, t-butyl orthoformate, other ortho-esters of carboxylic acids, dimethoxycyclohexane, other dialkoxycycloalkanes, triethyl borate, trioctyl borate, other orthoborates, and the like.

When used to increase the selectivity of the reaction, the dehydrating agents are used only in catalytic amounts, i.e., up to about 30 mole percent based on the weight of styrene used.

DETAILED DESCRIPTION OF THE INVENTION

The following examples represent specific methods of producing cinnamates according to the present invention.

EXAMPLE I

Styrene (53.0 g, 510 mmole), methanol (96.6 g, 3024 mmole), palladium (II) chloride (0.444 g, 2.5 mmole), and copper (I) chloride (2.475 g, 25 mmole) were charged into a 300 ml Hastelloy autoclave. After the autoclave was sealed, it was purged with a gas mixture containing 17% carbon monoxide in air by bubbling the gas mixture through the liquid contents of the autoclave while stirring for about 10 minutes. After that, the gas flow was adjusted to a 500 ml/min. flow rate, and the pressure in the reactor was adjusted to 500 psig with a back pressure regulator. The autoclave was then heated to 80° C., and the reaction was kept at this temperature for 4.0 hours.

After the reaction had gone to completion, the autoclave was cooled and the pressure was released. The reaction mixture was then analyzed using gas chromatography. Analysis of the reaction mixture showed the following products: dimethyl carbonate (8.4 mmole), dimethyl oxalate (0.6 mmole), acetophenone (91.8 mmole), methyl cinnamate (223.2 mmole), and dimethyl phenylsuccinate (2.1 mmole). This corresponds to 100% conversion of styrene with 43.7% selectivity to methyl cinnamate and 18% selectivity to acetophenone.

EXAMPLE II

The procedure of Example I was used, but the reaction temperature was changed to 120° C. The styrene was converted 100%, with 31.6% selectivity to acetophenone (161 mmole) and 333.3% selectivity to methyl cinnamate (170 mmole).

EXAMPLE III

The procedure of Example I was used, with a gas composition of 21% carbon monoxide in air and a reaction temperature of 60° C. There was obtained 100% conversion of styrene with 40.1% selectivity to methyl cinnamate (204 mmole) and 20.4% selectivity to acetophenone (104 mmole).

EXAMPLE IV

The procedure of Example I was used at a reaction temperature of 100° C. and 13% carbon monoxide in air. In this reaction, there was 100 conversation of styrene with 30.2% selectivity to methyl cinnamate (154 mmole) and 32.8% selectivity to acetophenone (167 mmole).

EXAMPLE V

In this Example, a stoichiometric amount of dehydrating agent was used for the reaction to increase the yield of methyl cinnamate over the yield of acetophenone. The total yield of valuable products, methyl cinnamate and acetophenone, was, however, decreased.

The procedure of Example IV was used with the addition of 503 mmole of 2,2-dimethoxypropane as a dehydrating agent. After the reaction had gone to completion, there was obtained 100% conversion of styrene with 50.7% selectivity to methyl cinnamate (259 mmole) and 4.3% selectivity to acetophenone (22 mole).

EXAMPLE VI

The procedure of Example V was repeated, except that only 180 mmole of 2,2-dimethoxypropane was used. In this experiment, we obtained 100% conversion of styrene with 53.8% selectivity to acetophenone (93 mmole).

It can be seen from a comparison of Example V and VI that only a catalytic amount of dehydrating agent relative to styrene is required to increase the yield of valuable products, methyl cinnamate and acetophenone, whereas a stoichiometric amount of dehydrating agent decreased the yield of valuable products.

The procedure of Example I can be used with ethanol, propanol, isopropanol, the butanols, pentanols, and hexanols to produce the corresponding cinnamates. The alcohol is used in quantities to give approximately 3000 mmole of alcohol to approximately 500 mmole of styrene. Where alcohols other than methanol are used, a small amount of dehydrating agent, up to 30 mole percent by weight of styrene, can be used to increase the selectivity of the reaction.

The catalysts that can be used in the process of the present invention can be any combination of compounds that give palladium (II) and copper. The valence of copper can be either I or II. The copper can be present in the form of a salt of either copper (I) or copper (II). The palladium can be present in the form of a salt or of any other compound that, under the reaction conditions, will yield of palladium (II) compound, including palladium black and palladium complex salts.

What is claimed is:

1. A method for the production of alkyl esters of cinnamic acid comprising the oxidative carbonylation of a styrene compound with carbon monoxide, oxygen, and an aliphatic alcohol in the presence of a catalytic amount of a catalyst consisting essentially of a palladium salt and a copper salt, and in the absence of a dehydrating agent.

2. The method of claim 1 wherein the aliphatic alcohol has from 1 to 6 carbon atoms.

3. The method of claim 1 wherein the styrene compound has the formula

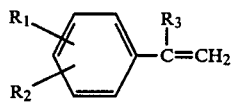

wherein $R_1$ and $R_2$ can be hydrogen, halogen, hydroxyl, alkyl, alkoxyl, aryl, aryloxyl, or nitro; and $R_3$ is hydrogen or an alkyl group of form 1 to 6 carbon atoms.

4. The method of claim 3 wherein the aliphatic alcohol has from 1 to 6 carbon atoms.

5. The method of claim 4 wherein the styrene is styrene.

6. The method of claim 5 wherein alcohol is methanol.

7. The method of claim 1 wherein the palladium salt is supported on a support selected from the group consisting of silica, silica-alumina, alumina, magnesia, titania, kieselguhr, active charcoal, and graphite.

8. The method of claim 1 wherein the palladium is supplied to the reaction in the form of palladium black.

9. The method of claim 1 wherein the palladium is supplied to the reaction in the form of palladium sponge.

10. The method of claim 1 wherein the copper salt is selected from the group consisting of copper (I) and copper (II) halides, copper (I) and copper (II) nitrates, copper (I) and copper (II) acetates, and copper (I) and copper (II) sulfates.

11. The method of claim 10 wherein the catalyst comprises palladium (II) chloride and copper (I) chloride.

* * * * *